United States Patent [19]

Prugh et al.

[11] Patent Number: 4,946,864

[45] Date of Patent: * Aug. 7, 1990

[54] HMG-COA REDUCTASE INHIBITORS

[75] Inventors: John Prugh, Chalfont; Albert A. Deana, Lansdale; Clarence S. Rooney, Worcester, all of Pa.

[73] Assignee: Merck & Co., Inc., Rahway, N.J.

[ * ] Notice: The portion of the term of this patent subsequent to Apr. 24, 2001 has been disclaimed.

[21] Appl. No.: 150,586

[22] Filed: Feb. 1, 1988

[51] Int. Cl.$^5$ .................. A61K 31/335; C07D 309/30
[52] U.S. Cl. .................... 514/460; 514/510; 549/292; 560/107; 560/119; 560/123; 562/405; 562/496; 562/501
[58] Field of Search ............... 514/460, 510; 549/292; 560/119

[56] References Cited

U.S. PATENT DOCUMENTS 4,444,784  4/1984  Hoffman et al. .............. 549/292
4,795,811  1/1989  Graham et al. ............... 549/292

Primary Examiner—Glennon H. Hollrah
Assistant Examiner—Ba K. Trinh
Attorney, Agent, or Firm—Melvin Winokur; Joseph F. DiPrima

[57] ABSTRACT

Novel HMG-CoA reductase inhibitors of formulae (I) and (II) are disclosed.

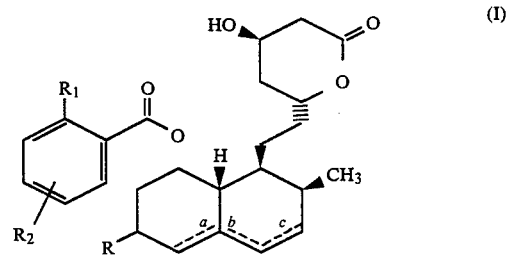

(I)

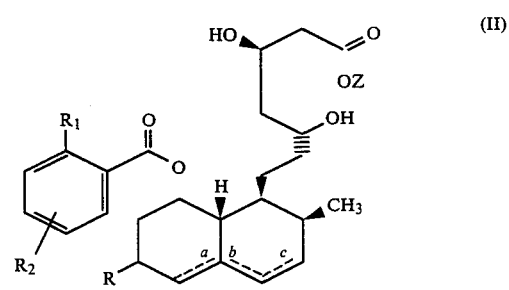

(II)

26 Claims, No Drawings

HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

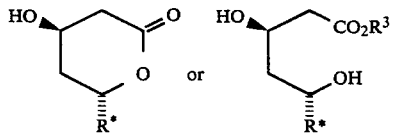

wherein:
$R^3$ is hydrogen, $C_{1-5}$ alkyl or $C_{1-5}$ alkyl substituted with a member of the group consisting of phenyl, dimethylamino, or acetylamino; and
$R^*$ is:

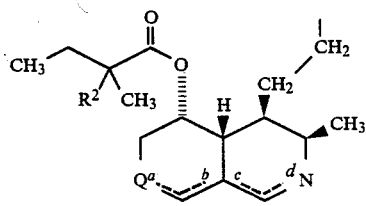

wherein Q is

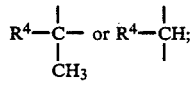

$R^4$ is H or OH; M is $CHR^5$, is H or OH; and
$R^2$ is hydrogen or methyl; and a, b, c, and d represent optional double bonds, especially where b and d represent double bonds or a, b, c, and d are all single bonds, provided that when a is a double bond, Q is

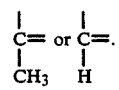

U.S. Pat. No. 4,444,784 discloses compounds of the above formula wherein $R^*$ is:

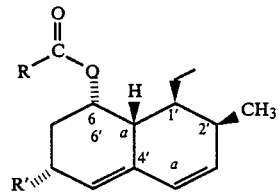

wherein R' is H or $CH_3$ and wherein amongst other groups R is phenyl or halophenyl where halo is chloro, fluoro, bromo or iodo. One compound 2, 4, $F_2—C_6H_3CO_2—$ is disclosed, but not prepared, in which the phenyl ring is ortho substituted.

Copending U.S. patent application Ser. No. 048,136 filed May 15, 1987, discloses compounds of the above formula wherein $R^*$ is:

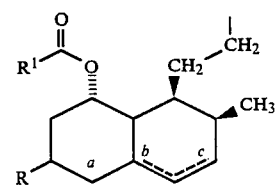

and R is $CH_2OH$ or $CO_2H$ and related alcoholic and carboxy derivatives and $R^1$ amongst other groups is phenyl or phenyl substituted with X and Y where X and Y are selected from a broad range of groups defined in claim 1.

DETAILED DESCRIPTION OF THE INVENTION

The HMG-CoA reductase inhibitors of the present invention are the compounds represented by the following general structural formula (I) & II:

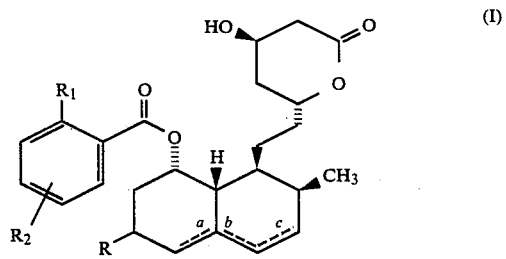
(I)

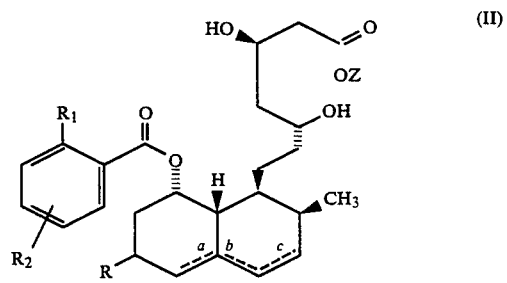
(II)

wherein R is

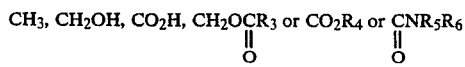

$R_1$ is $C_{1-3}$alkyl, haloC—$_{1-3}$alkyl, halo, $CF_3$, $C_{1-3}$alkylthio in the 2-position;

$R_2$ is hydrogen, $C_{1-3}$alkyl, $C_{2-4}$alkoxy in the 4- or or 5 position;

$R_3$ is $C_{1-5}$alkyl, phenyl or phenyl substituted with W;

$R_4$ is hydrogen or $C_{1-3}$alkyl or phenyl$C_{1-3}$alkyl or phenyl$C_{1-3}$alkyl in which the phenyl is substituted with W.

$R_5$ and $R_6$ are independently selected from hydrogen, $C_{1-3}$ alkyl, phenyl or substituted phenyl in which the substituent is W; halo and halogen are Cl or Br or F; and W is hydrogen, $C_{1-3}$alkyl, halogen, $C_{1-3}$alkoxy; hydroxy or hydroxy$C_{1-3}$alkyl;

Z is hydrogen, $C_{1-5}$alkyl or $C_{1-5}$alkyl substituted with a member of the group consisting of phenyl, dimethylamino or acetylamino;

a, b, and c are all single bonds or a and c are double bonds; or a pharmaceutically acceptable salt of the compounds of formula (II).

Except where specifically defined to the contrary, the terms "alkyl" and alkoxy include both the straight-chain and branched chain species of the term.

Illustrative of one embodiment of this invention are the compounds of formulae (I) and (II) wherein R is $CH_3$, $CO_2H$, or $CH_2OH$ and wherein formula (II) Z is hydrogen. In one class of this embodiment are the compounds wherein R is $CH_3$, and a and c are double bonds. In a subclass are the compounds wherein $R_1$ is $C_{1-3}$alkyl, halo, $CF_3$ or $C_{1-3}$ alkylthio and $R_2$ is H or $CH_3$, Exemplifying this embodiment are the following compounds:

(1) 6(R)- [2[(8(S)-(2-chlorobenzoyloxy) -2(S),6(R) -dimethy-1,2,6,7,8,8a(R)-hexahydronaphthyl-1(S)]-ethyl]-4(R)-hydroxy-3,4,5,6 -tetrahydro-2H -pyran-2-one or its corresponding free hydroxy acid.

(2) 6(R)-[2-[8(S)-(2-trifluoromethylbenzoyloxy)-2(S), 6(R) dimethyl 1,2,6,7,8,8a(R) hexahydronaphthyl-1-(S)]ethyl]-4(R)-hydroxy-3,4,5,6 tetrahydro-2H-pyran-2-one or the corresponding free hydroxy acid.

(3) 6(R)-[2-[8(S)-(2 methylbenzoyloxy)-2(S),6(R)-dimethyl-1,2,6,7,8,8a(R) hexahydronaphthyl -1(S)]e-thyl]-4(R)-hydroxy 3,4,5,6 tetrahydro 2H-pyran-2-one or the corresponding free hydroxy acid.

(4) 6(R)-[2-[8(S)-(2-methylthiobenzoyloxy)-2(S),6(R)-dimethyl-1,2,6,7,8,8a(R) hexahydronaphthyl-1(S)]-ethyl-4(R)-hydroxy-3,4,5,6-tetrahydro-2H -pyran-2-one or the corresponding free hydroxy acid.

(5) 6(R)-[2-[8(S)-(2-isopropylbenzoyloxy)-2(S),6(R) -dimethyl-1,2,6,7,8,8a(R) hexahydronaphthyl-1(S)]-ethyl-4(R)-hydroxy-3,4,5,6-tetrahydro-2H -pyran-2-one or the corresponding free hydroxy acid.

(6) 6(R)-[2-[8(S) -(2,5-dimethylbenzoyloxy)-2(S),6(R)-dimethyl-1,2,6,7,8,8a(R)-hexahydronaphthyl-1(S)]e-thyl]-4(R)-hydroxy-3,4,5,6-tetrahydro-2H-pyran-2-one.

Another embodiment of this invention are the compounds of formula (II) wherein Z is $C_{1-5}$ alkyl and pharmaceutically acceptable salts of the compounds of the formula (II), wherein Z is H.

The compounds of formula (I) wherein the 6-position of the polyhydronaphthyl ring contains a methyl group in the alpha configuration are prepared by hydrolysis of the 8 acyloxy group of lovastatin and protection of the lactone 4-hydroxy group as described in U.S. Pat. No. 4,444,784 followed by esterification of the napthyl ring 8-hydroxy group with an appropriate acyl halide following the lithium bromide activated acylation procedure in copending U.S. patent application Ser. No. 038,580 filed Apr. 18, 1987.

Alternatively the acylation can be accomplished following the standard acylation procedure in U.S. Pat. No. 4,444,784. The acyl halide can be prepared by standard reaction procedures from the available ortho substituted benzoic acids.

Compounds of formula (I) wherein R=$CH_2OH$ or $CO_2H$ or

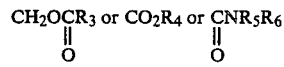

are prepared following the procedure detailed in copending U.S. patent application Ser. No. 048,136 filed May 15, 1987. An acyl halide formed from an appropriate ortho substituted benzoic acid is used in place of the acyl halides disclosed in the 048,136 reference.

Compounds of formula (I) wherein the 6-position of the polyhydronaphthyl ring contains a methyl group in the beta configuration are prepared from the corresponding 6-hydroxymethyl substituted analog following the procedure in copending U.S. patent application Ser. No. 092,354, filed Sept. 21, 1987.The 6-hydroxymethyl starting material is prepared following the procedure described in the above paragraph.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, $\alpha,\beta$-diaminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl-$C_{1-5}$alkyl, dimethylamino-$C_{2-5}$alkyl, or acetylamino-$C_{2-5}$alkyl may be employed if desired.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by a metathesis reaction.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the appropriate alcohol, benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents included dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Esters, of the carboxylic acids of formula (II), may also be obtained from the lactones of formula (I) by reaction of the lactone with an appropriate alkoxide employing the corresponding absolute alcohol as solvent.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in J. Med. Chem., 28, p. 347-358 (1985).

For estimation of relative inhibitory potencies, compacting (i.e., mevastatin) was assigned a value of 100 and the $IC_{50}$ value of the test compound was compared with that of compacting determined simultaneously in the published in vitro protocol.

Tabulated below for a number of the claimed compounds are relative potencies which are representative of the intrinsic HMG-CoA reductase inhibitory activities of the claimed compounds.

| Ar | Relative Potency |
|---|---|
| 2-CH₃-phenyl (CH₃) | 100 |
| 2-Cl-phenyl (Cl) | 87 |
| 2-SCH₃-phenyl (SCH₃) | 67 |
| 2-CH(CH₃)₂-phenyl (CH(CH₃)₂) | 54 |
| 2-CF₃-phenyl (CF₃) | 173 |
| 2,4-di-CH₃-phenyl (CH₃, CH₃) | 67 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100mg) which may be given in two to four divided doses. Higher doses may be favorably employed as required.

The compounds of this invention may also be coadministered with pharmaceutically acceptable nontoxic cationic polymers capable of binding bile acids in a non reabsorbable form in the gastrointestinal tract. Examples of such polymers include cholestyramine, colestipol and poly (methyl-(3 trimethylaminopropyl)imino trimethylene dihalide). The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[(8(S)-(2-chlorobenzoyloxy)-2-(S),6(R)-dimethyl-1,2,6,7,8,8a(R)-hexahydronaphthyl-1-(S)]ethyl]-4(R)-hydroxy-3,4,5,6-tetahydro-2H pyran-2-one.

(a)
6(R)-[2-[(8(S)-(2-chlorobenzoyloxy)-2-(S),6(R)-dimethyl-1,2,6,7,8,8a(R)-hexahydronaphthyl-1(S)]-ethyl]-4(R)-tert-butyldimethylsilyloxy-3,4,5,6-tetrahydro-2H-pyran-2-one (1a)

2-Chlorobenzoyl chloride (1.17 g, 0.0067 mol) was added to a solution of 6(R)-[2-[8(S)-hydroxy-2(S),6(R) dimethyl-1,2,6,7,8,8a(R) -hexahydronaphthyl-1(S)]ethyl]-4(R)-tert butyldimethylsilyloxy-3,4,5,6,-tetrahydro-2H-pyran-2-one(1.0 g, 0.0073 mol) in pyridine (1 ml) containing 4-pyrrolidinopyridine (0.04 g). The mixture was stirred at 90° C. under a nitrogen atmosphere for 4 hours, at which time TLC (silica gel, 50% ether/hexanes) indicated that the reaction was essentially complete. After cooling to room temperature water (3 ml) was added and the mixture stirred for 15 minutes. The reaction mixture was then poured into diethyl ether and the ether phase washed with water (3x), dilute HCl, water, saturated aqueous NaHCO$_3$, and saturated brine. After filtration the ether solution was evaporated to dryness. The yellow oil which resulted was chromatographed on silica gel (230-400 mesh) employing 45% ether/hexanes as a developing solvent. The product was isolated as a colorless viscous oil. TLC (silica gel, 45% ether/hexanes showed a single spot of R$_f$=0.33. The 'H NMR spectrum was consistent with the expected structure.

(b) Preparation of
6(R)-[2-[(8(S)-(2-chlorobenzoyl-oxy)-2(S),6(R)-dimethyl-1,2,6,7,8,8a(R)-hexahydro-naphthyl-1(S)]ethyl]-4(R)-hydroxy-3,4,5,6-tetrahydro-2H-pyran-2-one (1b)

A solution of tetrabutylammonium fluoride in THF (1M, 13 ml, 0.013 mol) was added dropwise to a THF (dry) solution of the product from step 1(a) (1.02 g, 0.0018 mol) in dry THF (6 ml) containing HOAc (1 ml, 0.018 mol). The clear solution was stirred overnight for about 17 hours at ambient temperature. Diethyl ether (200 ml) was added to the mixture and the ether phase washed with dilute HCl, H$_2$O, brine and then dried over MgSO$_4$. Evaporation gave a solid residue which was crystallized from diethyl ether. A second recrystallization from ether gave a pure product of M.P. 159°-162° C. 'H NMR (300 MHz, CDCl$_3$) δ 0.93 (d, J=6.5Hz, 3H), 1.05 (d, J=7Hz, 3H), 1.18-1.55 (m, 3H), 1.8-2.1 (m, 5H), 2.22 (dd, J=14.5, 3.5Hz, 1H), 2.33-2.62 (m, 4H), 2.69 (dd, J=17, 5.5Hz, 1H), 4.32 (m, 1H), 4.63 (m, 1H), 5.56 (bs, 1H), 5.62 (m, 1H), 5.82 (dd, J=9, 6Hz, 1H), 7.28-7.35 (m, 1H), 7.36-7.48 (m, 2H), 7.76 (dd, J=7, 1Hz, 1H).

Elemental Analysis Calc'd for C$_{26}$H$_{31}$ClO$_5$ C, 68.04; H, 6.81. Found: C, 67.97; H, 7.23.

EXAMPLE 2

Preparation of
6(R)-[2-[8(S)-(2-trifluormethyl-benzoyloxy)-2(S),6(R)-dimethyl-1,2,6,7,8,8a(R)-hexa-hydronaphthyl-1(S)]ethyl]-4(R)-hydroxy-3,4,5,6-tetrahydro-2H-pyran-2-one.

(a) Preparation of
6(R)-[2-[8(S)-(2-trifluoromethyl-benzoyloxy)-2(S),6(R) dimethyl
1,2,6,7,8,8a(R)-hexahydronaphthyl-1(S)]ethyl]-4(R)-tert-butyl
-dimethylsilyloxy-3,4,5,6-tetrahydro-2H-pyran-2-one
(2a)

Anhydrous LiBr (0.51 g, 0.006 mol) was added to a solution of 2-trifluoromethylbenzoyl chloride (0.63 g, 0.003 mol) in pyridine (6 ml). After stirring at room temperature for 20 minutes followed by heating for about 5 minutes at 80° C. the mixture was allowed to cool to room temperature. 4-Pyrrolidinopyridine (0.06 g) was added followed by 6(R)-[2-[8(S)-hydroxy-2(S),6(R)-dimethyl-1,2,6,7,8,8a(R)-hexahydronaphthyl-1(S)]ethyl]-4(R)-tert butyldimethylsilyloxy-3,4,5,6-tetrahydro-2H -pyran-2-one. (0.62 g, 0.0014 mol). The mixture was heated at 90° C. for 15 hours. After cooling to room temperature, the reaction mixture was poured into diethyl ether and water. The ether phase washed with H$_2$O (3x), dilute HCl, H$_2$O, saturated aqueous NaHC$_3$, and saturated brine. After filtration the ether solution was evaporated to dryness. The yellow oil was chromatographed on silica gel (230-400 mesh) employing 20% ethyl acetate/hexanes as a developing solvent. The colorless oil isolated gave a single spot by TLC with R$_f$=0.36 using 20% ether/hexane. The $^1$H NMR spectrum was consistent with the desired structure.

(b) Preparation of
6(R)-[2-[8(S)-(2-trifluormethyl-benzoyloxy)-2(S),6(R)-dimethyl-1,2,6,7,8,8a(R)-hexahydronaphthyl-1(S)]ethyl]-4(R) hydroxy- 3,4,-5,6 tetrahydro-2H
-pyran-2-one (2b)

The tert-butyldimethylsilyloxy protecting group of the compound of 2(a) was cleaved using the procedure and the same molar relationships as in Example 1(b):

'H NMR (300 MHz, CDCl$_3$) δ 0.95 (d, J=8Hz, 3H), 1.03 (d, J=8Hz, 3H), 1.3-1.54 (m, 2H), 1.6-1.73 (m, 1H), 1.8-2.1 (m, 5H), 2.2 (dd, J=15, 3Hz, 1H), 2.35-2.54 (m, 3H). 2.6 (dd, J=15, 3Hz. 1H), 2.7 (dd, J=5, 18Hz, 1H). 4.33 (m, 1H), 4.62 (m, 1H), 5.81 (m, 1H), 6.0 (d, J=10Hz, 1H), 7.6 (m, 2H), 7.7 (m, 1H), 7.76 (m, 1H).

Elemental Analysis Calc'd for C$_{27}$H$_{31}$F$_3$O$_5$0.1CH$_2$Cl$_2$ C, 64.96; H, 6.28. Found: C, 64.61; H, 6.32.

EXAMPLE 3

Preparation of 6(R)-[2-[8(S)-(2-methylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (3a)

The titled compound was prepared following the procedure and molar amounts of Example 1 but substituting 2-methylbenzoyl chloride for the acyl halide.

$^1$H NMR (300 MHz, CDCl$_3$) δ 0.92 (d, J=6Hz, 3H), 1.0 (d, J=6Hz, 3H), 1.1–1.7 (m, 3H), 1.72–1.93 (m, 4H), 2.01 (ddd, J=15, 9, 3Hz, 1H), 2.10 (dd, J=15, 4Hz, 1H), 2.32–2.57 (m, 4H), 2.59–2.68 (m, 4H), 4.25 (m, 1H), 4.57 (m, 1H), 5.57 (m, 2H), 5.82 (dd, J=15.5, 6Hz, 1 H), 6.04 (d, J=9Hz, 1 H), 7.2–7.27 (m, 2H), 7.4 (t, J=7.5Hz, 1H), 7.89 (d, J=7.5Hz, 1H).

Elemental Analysis Calc'd for C$_{27}$H$_{34}$O$_5$·0.5H$_2$O C, 72.46; H, 7.88. Found: C, 72.64; H, 7.69.

EXAMPLE 4

Preparation of 6(R)-[2-[8(S)-(2-methylthiobenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (4a)

The titled compound was prepared following the procedure and molar amounts of Example 2 substituting 2 methylthiobenzoyl chloride for the acyl halide.

$^1$H NMR (300 MHz, CDCl$_3$) δ 0.9 (d, J=7Hz, 3H), 1.05 (d, J=8Hz, 3H), 1.17–1.3 (m, 1H), 1.32–1.5 (m, 1H), 1.5–1.6 (m, 2H), 1.73–2.1 (m, 5H), 2.12–2.23 (m, 1H), 2.33–2.59 (m, 6H), 2.65 (dd, J=16, 6Hz, 1H), 4.18 (m, 1H), 4.56 (m, 1H), 5.62 (m, 2H), 5.82 (dd, J=10, 5Hz, 1H), 6.07 (d, J=10Hz, 1 H), 7.2 (m, 1H), 7.3 (m, 1H), 7.51 (m, 1H), 7.98 (d, J=8Hz, 1H).

Elemental Analysis Calc'd for C$_{27}$H$_{34}$O$_5$S C, 68.91; H, 7.28. Found: C, 69.05; H, 7.51.

EXAMPLE 5

Preparation of 6(R)-[2-[8(S)-(2-isopropylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one The titled compound was prepared following the procedure and molar amounts of Example 2 substituting 2-isopropylbenzoyl chloride for the acyl halide.

$^1$H NMR (300 MHz, CDCl$_3$) δ 0.93 (d, J=8Hz, 3H), 1.01 (d, J=8Hz, 3H), 1.22 (d, J=8Hz, 3H), 1.28 (d, J=7Hz, 3H), 1.3–1.7 (m, 3H), 1.8–2.09 (m, 4H), 2.2 (dd, J=16, 3Hz, 1H), 2.31–2.61 (m, 4H), 2.78 (dd, J=17, 5Hz, 1H), 3.8 (pentet, J=8Hz, 1H), 4.3 (m, 1H), 4.6 (m, 1H), 5.57 (m, 2H), 5.82 (dd, J=10, 7Hz, 1H), 6.03 (d, J=10Hz, 1H), 7.2 (m, 1H), 7.43 (m, 2H), 7.68 (d, J=8Hz, 1H).

Elemental Analysis Calc'd for C$_{29}$H$_{38}$O$_5$ C, 74.65; H, 8.21. Found: C, 74.70; H, 8.52.

EXAMPLE 6

Preparation 6(R)-[2-[8(S)-(2,5-dimethylbenzoyloxy)2(S),6(R)-dimethyl-1,2,6,7,8,8a(R)-hexahydronaphthyl-1(S)]ethyl]-4(R)-hydroxy-3,4,5,6 tetrahydro 2H-pyran-2-one The above compound is prepared following the procedure of Example 1 substituting 2,5-dimethylbenzoyl chloride for the acyl halide.

EXAMPLE 7

Preparation of Ammonium Salts of Compounds II

To lactone (1.0 mmol) from Example 1 Step b, in ethanol solution, is added with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give the ammonium salt.

EXAMPLE 8

Preparation of Alkali and Alkaline Earth Salts of Compounds II

To a solution of 49 mg of lactone from Example 1 Step b in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of Ca(OH)$_2$.

EXAMPLE 9

Preparation of Ethylenediamine Salts of Compounds II

To a solution of 0.50 g of the ammonium salt from Example 7 in 10 ml of methanol is added 0.06 ml of ethylenediamine. The methanol is stripped off under vacuum to obtain the desired ethylenediamine salt.

EXAMPLE 10

Preparation of Tris(hydroxymethyl)aminomethane Salts of Compounds II

To a solution of 202 mg of the ammonium salt from Example 7 in 5 ml of methanol is added a solution of 50 mg of tris(hydroxymethyl)aminomethane in 5 ml of methanol. The solvent is removed in vacuo to afford the desired tris(hydroxymethyl)aminomethane salt.

EXAMPLE 11

Preparation of L-Lysine Salts of Compounds II

A solution of 0.001 mole of L-lysine and 0.0011 mole of the ammonium salt from Example 7 in 15 ml of 85% ethanol is concentrated to dryness in vacuo to give the desired L-lysine salt.

Similarly prepared are the L-arginine, L-ornithine, and the α,β-diaminobutyric acid salts.

EXAMPLE 12

Preparation of Tetramethylammonium Salts of Compounds II

A mixture of 68 mg of ammonium salt from Example 7 in 2 ml of methylene chloride and 0.08 ml of 24% tetramethylammonium hydroxide in methanol is concentrated to dryness to yield the desired tetramethylammonium salt.

EXAMPLE 13

Preparation of Methyl Esters of Compounds II

To a solution of 400 mg of lactone from Example 1 Step b in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried (Na$_2$SO$_4$), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenylethanol, 2-acetamidoethanol and the like, and employing the corresponding alcohol as solvent the corresponding esters are obtained.

EXAMPLE 14

Preparation of Free Dihydroxy Acids

The sodium salt of the compound II from Example 8 is dissolved in 2 ml of ethanol water (1:1; v:v) and added to 10 ml of 0.1N hydrochloric acid from which the dihydroxy acid is extracted with ethyl acetate. The organic extract is washed once with water, dried (Na$_2$SO$_4$), and evaporated in vacuo with a bath temperature not exceeding 30° C. The dihydroxy acid derivative derived slowly reverts to the corresponding parent lactone on standing at room temperature.

EXAMPLE 15

As a specific embodiment of a composition of this invention, 20 mg of lactone from Example 1 Step b is formulated with sufficient finely divided lactose to provide a total amount of 580 to 590 mg to fill a size 0, hard-gelatin capsule.

What is claimed is:

1. A compound represented by structural formula (I'):

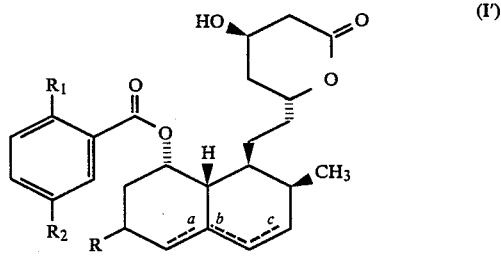

R is

CH$_3$, CH$_2$OH, CO$_2$H, or CH$_2$OCR$_3$ or CO$_2$R$_4$ or CNR$_5$R$_6$;
$\quad\quad\quad\quad\quad\quad\quad\quad\quad$ ‖ $\quad\quad\quad\quad\quad\quad$ ‖
$\quad\quad\quad\quad\quad\quad\quad\quad\quad$ O $\quad\quad\quad\quad\quad\quad\quad$ O R$_1$ is C$_{1-3}$alkyl, C$_{1-3}$alkoxy, chlorine or bromine, CF$_3$, or C$_{1-3}$alkylthio;
R$_2$ is H, C$_{1-3}$alkyl or C$_{2-4}$alkoxy;
R$_3$ is C$_{1-5}$alkyl, phenyl, or phenyl substituted with W;
R$_4$ is H, C$_{1-3}$alkyl, phenylC$_{1-3}$alkyl or phenyl C$_{1-3}$alkyl in which the phenyl is substituted with W;
R$_5$ and R$_6$ are independently selected from hydrogen, C$_{1-3}$alkyl, phenyl or substituted phenyl in which the substituent is W;
a, b, c are all single bonds or a and c are double bonds; and
W is H, C$_{1-3}$alkyl, chlorine, bromine, fluorine, C$_{1-3}$alkyl, hydroxy or hydroxyC$_{1-3}$alkyl.

2. A compound of claim 1, wherein R is methyl, or CH$_2$OH, CO$_2$H,.

3. A compound of claim 2 wherein R is methyl.

4. A compound of claim 3 wherein a and c are double bonds.

5. A compound of claim 4 wherein R$_1$ is C$_{1-3}$alkyl, chlorine, CF$_3$ or C$_{1-3}$alkylthio.

6. A compound of claim 5 wherein R$_2$ is H or methyl.

7. A compound of claim 6 wherein R$_2$ is hydrogen.

8. A compound of claim 7 which is 6(R)-[2-[(8(S)-(2-chlorobenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

9. A compound of claim 7 which is 6(R)-[2-[8(S)-(2-trifluoromethylbenzoyloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one.

10. A compound of claim 7 which is 6(R)-[2-[(S)-(2-methylbenzoyloxy)-2(S), 6(R)-dimethyl-1,2,6,7,8,8a(R)-hexahydronaphthyl-1(S)]ethyl]-4(R)-hydroxy-3,4,5,6-tetrahydro-2H-pyran-2-one.

11. A compound of claim 7 which is 6(R) -2-[(S)-(2-methylthiobenzoyloxy)-2(S), 6(R)-dimethyl-1,2,6,7,8,8a(R)-hexahydronaphthyl-1(S)]ethyl-4(R)- hydroxy-3,4,5,6,-tetrahydro-2H -pyran-2-one.

12. A compound of claim 7 which is 6(R)-[2-[(S)-(2-isopropylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

13. A hypocholesterolemic, hypolipidemic pharmaceutical composition comprising a nontoxic therapeutically effective amount of a compound of claim 1 and a pharmaceutically effective carrier.

14. A composition according to claim 13 wherein R is CH$_3$, CH$_2$OH or CO$_2$H.

15. A composition of claim 14 wherein R is CH$_3$.

16. A composition of claim 15 wherein R$_2$ is hydrogen and R$_1$ is C$_{1-3}$alkyl, chlorine, CF$_3$ or C$_{1-3}$alkylthio.

17. A composition according to claim 16 in which the therapeutically active ingredient is selected from:
   a. 6(R)-[2-[(8(S)-(2-chlorobenzoyloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one;
   b. 6(R)-[2-[(S)-(2-trifluoromethylbenzoyloxy)-2(S),6(R)-dimethyl-1,2,6,7,8,8a(R)-hexahydronaphthyl-1(S)]ethyl]-4(R)-hydroxy-3,4,5,6,-tetrahydro-2H-pyran-2-one;
   c. 6(R)-[2-[(S)-(2-methylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one
   d. 6(R)-[2-[(S)-(2-methylthiobenzoyloxy)-2(S), 6(R)-dimethyl-1,2,6,7,8,8a(R)-hexhydronaphthyl-1(S)]-ethyl]-4(R)- hydroxy-3,4,5,6-tetrahydro-2H-pyran-2-one,
   e. 6(R)-[2-[(S)-(2-isopropylbenzoyloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one.

18. A hypocholesterolemic, hypolipidemic pharmaceutical composition comprising a nontoxic therapeutically effective amount of a compound of claim 1 in combination with a pharmaceutically acceptable nontoxic polymer capable of binding bile acids in a non-reabsorbable form in the gastrointestinal tract and a pharmaceutically acceptable carrier.

19. A method of inhibiting cholesterol biosynthesis comprising the administration to a subject in need of such treatment a nontoxic therapeutically effective amount of a compound of claim 1.

20. A method according to claim 19 wherein R is $CH_3$, $CH_2OH$ or $CO_2H$.

21. A method according to claim 20 wherein R is $CH_3$.

22. A method according to claim 21 wherein $R_2$ is hydrogen and $R_1$ is $C_{1-3}$alkyl, chlorine, $CF_3$ or $C_{1-3}$alkylthio.

23. A method according to claim 22 wherein the therapeutically effective ingredient is selected from:
   a. 6(R)-[2-[(8(S)-(2-chlorobenzoyloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one;
   b. 6(R)-[2-[8(S)-(2-trifluoromethylbenzoyloxy)-2(S),6(R)-dimethyl-1,2,6,7,8,8a(R)-hexahydronaphthyl-1(S)ethyl]-4(R)-hydroxy-3,4,5,6-tetrahydro -2H-pyran-2-one;
   c. 6(R)-[2-[8(S)-(2-methylbenzoyloxy-2(S),6(R)-dimethyl-1,2,6,7,8,8a (R)-hexahydronaphthyl-1(S)]ethyl]-4(R)-hydroxy-3,4,5,6-tetrahydro-2H-pyran-2-one;
   d. 6(R)-[2-[8(S)-(2-methylthiobenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran -2-one;
   e. 6(R)-[2-[8(S)-(2-isopropylbenzoyloxy)-2(S),6(R)-dimethyl-1,2,6,7,8, 8a(R)-hexahydronaphthyl-1(S)]ethyl]-4(R)-hydroxy-3,4,5,6-tetrahydro-2H-pyran-2-one.

24. A compound of claim 6 which is:
6(R)-[2-[8(S)-(2,5-dimethylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

25. A composition according to claim 15 in which the therapeutically active ingredient is:
6(R)-[2-[8(S)-(2,5-dimethylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

26. A method according to claim 21 wherein the therapeutically effective ingredient is: 6(R)-[2[8(S)-(2,5-dimethylbenzoyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

* * * * *